(12) United States Patent
Humphrey et al.

(10) Patent No.: US 11,207,499 B2
(45) Date of Patent: Dec. 28, 2021

(54) STEERABLE CATHETER

(71) Applicant: Edwards Lifesciences Corporation, Irvine, CA (US)

(72) Inventors: Timothy Lee Humphrey, Cypress, CA (US); Michael R. Bialas, Lake Forest, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 702 days.

(21) Appl. No.: 16/159,966

(22) Filed: Oct. 15, 2018

(65) Prior Publication Data

US 2019/0117937 A1  Apr. 25, 2019

Related U.S. Application Data

(60) Provisional application No. 62/574,875, filed on Oct. 20, 2017.

(51) Int. Cl.
*A61M 25/01* (2006.01)
*A61B 1/005* (2006.01)
(Continued)

(52) U.S. Cl.
CPC ....... *A61M 25/0147* (2013.01); *A61B 1/0052* (2013.01); *A61B 1/0057* (2013.01); *A61M 25/0136* (2013.01); *A61B 2017/003* (2013.01); *A61B 2017/00327* (2013.01); *A61B 2018/00369* (2013.01); *A61M 25/0053* (2013.01); *A61M 2025/015* (2013.01)

(58) Field of Classification Search
CPC .......... A61M 25/0147; A61M 25/0133; A61M 25/0136; A61B 2017/003; A61M 2017/00327

See application file for complete search history.

(56) References Cited

U.S. PATENT DOCUMENTS

| 519,297 A | 5/1894 | Bauer |
|---|---|---|
| 4,035,849 A | 7/1977 | Angell et al. |

(Continued)

FOREIGN PATENT DOCUMENTS

| DE | 19532846 A1 | 3/1997 |
|---|---|---|
| DE | 19907646 A1 | 8/2000 |

(Continued)

*Primary Examiner* — Jenna Zhang
(74) *Attorney, Agent, or Firm* — Klarquist Sparkman, LLP; Joel B. German (57) ABSTRACT

A steerable medical apparatus includes a shaft, a steering mechanism, and an actuation mechanism. The shaft has a proximal portion, a distal portion, a first pull wire, and a second pull wire. The distal ends of the first and second pull wires are coupled to the distal portion of the shaft. The steering mechanism has a first wheel and a second wheel coupled by a differential mechanism. The proximal ends of the first and second pull wires are respectively coupled to the first and second wheels. The actuation mechanism is coupled to the steering mechanism. Actuating the actuation mechanism in a first operational mode causes the distal portion of the shaft to curve in a first plane. Actuating the actuation mechanism in a second operational mode causes the distal portion of the shaft to curve away from the first plane.

20 Claims, 3 Drawing Sheets

(51) Int. Cl.
  *A61B 18/00* (2006.01)
  *A61B 17/00* (2006.01)
  *A61M 25/00* (2006.01)

(56) References Cited

U.S. PATENT DOCUMENTS

| | | | |
|---|---|---|---|
| 4,592,340 A | 6/1986 | Boyles |
| 4,955,895 A | 9/1990 | Sugiyama et al. |
| 4,994,077 A | 2/1991 | Dobben |
| 5,059,177 A | 10/1991 | Towne et al. |
| 5,176,698 A | 1/1993 | Burns et al. |
| 5,192,297 A | 3/1993 | Hull |
| 5,266,073 A | 11/1993 | Wall |
| 5,325,845 A | 7/1994 | Adair |
| 5,358,496 A | 10/1994 | Ortiz et al. |
| 5,411,552 A | 5/1995 | Andersen et al. |
| 5,554,185 A | 9/1996 | Block et al. |
| 5,591,195 A | 1/1997 | Taheri et al. |
| 5,599,305 A | 2/1997 | Hermann et al. |
| 5,632,760 A | 5/1997 | Sheiban et al. |
| 5,639,274 A | 6/1997 | Fischell et al. |
| 5,728,068 A | 3/1998 | Leone et al. |
| 5,749,890 A | 5/1998 | Shaknovich |
| 5,782,809 A | 7/1998 | Umeno et al. |
| 5,824,044 A | 10/1998 | Quiachon et al. |
| 5,840,081 A | 11/1998 | Andersen et al. |
| 5,908,405 A | 6/1999 | Imran et al. |
| 5,916,147 A | 6/1999 | Boury |
| 5,954,654 A * | 9/1999 | Eaton .................. A61B 1/0052 600/462 |
| 5,961,536 A | 10/1999 | Mickley et al. |
| 5,968,068 A | 10/1999 | Dehdashtian et al. |
| 6,019,777 A | 2/2000 | Mackenzie |
| 6,027,510 A | 2/2000 | Alt |
| 6,033,381 A | 3/2000 | Kontos |
| 6,143,016 A | 11/2000 | Bleam et al. |
| 6,162,208 A | 12/2000 | Hipps |
| 6,168,614 B1 | 1/2001 | Andersen et al. |
| 6,174,327 B1 | 1/2001 | Mertens et al. |
| 6,217,585 B1 | 4/2001 | Houser et al. |
| 6,235,050 B1 | 5/2001 | Quiachon et al. |
| 6,251,092 B1 | 6/2001 | Qin et al. |
| 6,379,372 B1 | 4/2002 | Dehdashtian et al. |
| 6,383,171 B1 | 5/2002 | Gifford et al. |
| 6,454,799 B1 | 9/2002 | Schreck |
| 6,458,153 B1 | 10/2002 | Bailey et al. |
| 6,461,382 B1 | 10/2002 | Cao |
| 6,471,672 B1 | 10/2002 | Brown et al. |
| 6,500,147 B2 | 12/2002 | Omaleki et al. |
| 6,514,228 B1 | 2/2003 | Hamilton et al. |
| 6,527,979 B2 | 3/2003 | Constantz et al. |
| 6,579,305 B1 | 6/2003 | Lashinski |
| 6,582,462 B1 | 6/2003 | Andersen et al. |
| 6,652,578 B2 | 11/2003 | Bailey et al. |
| 6,730,118 B2 | 5/2004 | Spenser et al. |
| 6,733,525 B2 | 5/2004 | Yang et al. |
| 6,764,504 B2 | 7/2004 | Wang et al. |
| 6,767,362 B2 | 7/2004 | Schreck |
| 6,830,584 B1 | 12/2004 | Seguin |
| 6,893,460 B2 | 5/2005 | Spenser et al. |
| 6,908,481 B2 | 6/2005 | Cribier |
| 7,011,094 B2 | 3/2006 | Rapacki et al. |
| 7,018,406 B2 | 3/2006 | Seguin et al. |
| 7,018,408 B2 | 3/2006 | Bailey et al. |
| 7,137,993 B2 | 11/2006 | Acosta et al. |
| 7,276,084 B2 | 10/2007 | Yang et al. |
| 7,318,278 B2 | 1/2008 | Zhang et al. |
| 7,320,702 B2 | 1/2008 | Hammersmark et al. |
| 7,320,704 B2 | 1/2008 | Lashinski et al. |
| 7,374,571 B2 | 5/2008 | Pease et al. |
| 7,393,360 B2 | 7/2008 | Spenser et al. |
| 7,435,257 B2 | 10/2008 | Lashinski et al. |
| 7,510,575 B2 | 3/2009 | Spenser et al. |
| 7,585,321 B2 | 9/2009 | Cribier |
| 7,594,926 B2 | 9/2009 | Linder et al. |
| 7,597,709 B2 | 10/2009 | Goodin |
| 7,618,446 B2 | 11/2009 | Andersen et al. |
| 7,780,723 B2 | 8/2010 | Taylor |
| 7,785,366 B2 | 8/2010 | Maurer et al. |
| 7,959,661 B2 | 6/2011 | Hijlkema et al. |
| 8,029,556 B2 | 10/2011 | Rowe |
| 8,167,932 B2 | 5/2012 | Bourang et al. |
| RE43,882 E | 12/2012 | Hopkins et al. |
| 8,449,606 B2 | 5/2013 | Eliasen et al. |
| 8,475,523 B2 | 7/2013 | Duffy |
| 8,568,472 B2 | 10/2013 | Marchand et al. |
| 9,061,119 B2 | 6/2015 | Le et al. |
| 9,119,716 B2 | 9/2015 | Lee et al. |
| 9,795,477 B2 | 10/2017 | Tran et al. |
| 2001/0002445 A1 | 5/2001 | Vesely |
| 2001/0007082 A1 | 7/2001 | Dusbabek et al. |
| 2002/0032481 A1 | 3/2002 | Gabbay |
| 2002/0058995 A1 | 5/2002 | Stevens |
| 2002/0165461 A1 | 11/2002 | Hayzelden et al. |
| 2003/0040792 A1 | 2/2003 | Gabbay |
| 2003/0050694 A1 | 3/2003 | Yang et al. |
| 2003/0120341 A1 | 6/2003 | Shennib et al. |
| 2004/0093061 A1 | 5/2004 | Acosta et al. |
| 2004/0133263 A1 | 7/2004 | Dusbabek et al. |
| 2004/0143197 A1 | 7/2004 | Soukup et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0080474 A1 | 4/2005 | Andreas et al. |
| 2005/0096736 A1 | 5/2005 | Osse et al. |
| 2005/0137689 A1 | 6/2005 | Salahieh et al. |
| 2005/0149160 A1 | 7/2005 | McFerran |
| 2005/0203614 A1 | 9/2005 | Forster et al. |
| 2005/0203617 A1 | 9/2005 | Forster et al. |
| 2005/0245894 A1 | 11/2005 | Zadno-Azizi |
| 2006/0025857 A1 | 2/2006 | Bergheim et al. |
| 2006/0282150 A1 | 12/2006 | Olson et al. |
| 2007/0005131 A1 | 1/2007 | Taylor |
| 2007/0073389 A1 | 3/2007 | Bolduc et al. |
| 2007/0088431 A1 | 4/2007 | Bourang et al. |
| 2007/0112422 A1 | 5/2007 | Dehdashtian |
| 2007/0203575 A1 | 8/2007 | Forster et al. |
| 2007/0219612 A1 | 9/2007 | Andreas et al. |
| 2007/0239254 A1 | 10/2007 | Chia et al. |
| 2007/0244546 A1 | 10/2007 | Francis |
| 2007/0265700 A1 | 11/2007 | Eliasen et al. |
| 2008/0065011 A1 | 3/2008 | Marchand et al. |
| 2008/0125853 A1 | 5/2008 | Bailey et al. |
| 2008/0294230 A1 | 11/2008 | Parker |
| 2009/0024428 A1 | 1/2009 | Hudock, Jr. |
| 2009/0069889 A1 | 3/2009 | Suri et al. |
| 2009/0138079 A1 | 5/2009 | Tuval et al. |
| 2009/0157175 A1 | 6/2009 | Benichou |
| 2009/0192585 A1 | 7/2009 | Bloom et al. |
| 2009/0228093 A1 | 9/2009 | Taylor et al. |
| 2009/0276040 A1 | 11/2009 | Rowe et al. |
| 2009/0281619 A1 | 11/2009 | Le et al. |
| 2009/0299456 A1 | 12/2009 | Melsheimer |
| 2009/0319037 A1 | 12/2009 | Rowe et al. |
| 2010/0030318 A1 | 2/2010 | Berra |
| 2010/0036472 A1 | 2/2010 | Papp |
| 2010/0036473 A1 | 2/2010 | Roth |
| 2010/0049313 A1 | 2/2010 | Alon et al. |
| 2010/0076402 A1 | 3/2010 | Mazzone et al. |
| 2010/0076541 A1 | 3/2010 | Kumoyama |
| 2010/0082089 A1 | 4/2010 | Quadri et al. |
| 2010/0094394 A1 | 4/2010 | Beach et al. |
| 2010/0121425 A1 | 5/2010 | Shimada |
| 2010/0145431 A1 | 6/2010 | Wu et al. |
| 2010/0161036 A1 | 6/2010 | Pintor et al. |
| 2010/0174363 A1 | 7/2010 | Castro |
| 2010/0198347 A1 | 8/2010 | Zakay et al. |
| 2010/0274344 A1 | 10/2010 | Dusbabek et al. |
| 2011/0015729 A1 | 1/2011 | Jimenez et al. |
| 2011/0054596 A1 | 3/2011 | Taylor |
| 2011/0137331 A1 | 6/2011 | Walsh et al. |
| 2011/0160846 A1 | 6/2011 | Bishop et al. |
| 2012/0123529 A1 | 5/2012 | Levi et al. |
| 2012/0239142 A1 | 9/2012 | Liu et al. |

(56) References Cited

U.S. PATENT DOCUMENTS

| | | |
|---|---|---|
| 2013/0030519 A1 | 1/2013 | Tran et al. |
| 2013/0131592 A1* | 5/2013 | Selkee ............... A61M 25/0136 604/95.04 |
| 2013/0317598 A1 | 11/2013 | Rowe et al. |
| 2014/0296962 A1 | 10/2014 | Cartledge et al. |
| 2016/0074625 A1* | 3/2016 | Furnish ............. A61M 25/0136 604/95.04 |
| 2017/0065415 A1 | 3/2017 | Rupp et al. |
| 2017/0326337 A1* | 11/2017 | Romoscanu ....... A61B 18/1492 |
| 2018/0153689 A1 | 6/2018 | Maimon et al. |
| 2018/0256851 A1* | 9/2018 | Edminster ......... A61M 25/0097 |
| 2018/0264231 A1* | 9/2018 | Scheibe ............ A61M 25/0133 |
| 2018/0344456 A1 | 12/2018 | Barash et al. |

FOREIGN PATENT DOCUMENTS

| | | |
|---|---|---|
| EP | 0592410 B1 | 10/1995 |
| EP | 0850607 A1 | 7/1998 |
| FR | 2815844 A1 | 5/2002 |
| WO | 9117720 A1 | 11/1991 |
| WO | 0149213 A2 | 7/2001 |
| WO | 0154625 A1 | 8/2001 |
| WO | 0176510 A2 | 10/2001 |
| WO | 0222054 A1 | 3/2002 |
| WO | 0236048 A1 | 5/2002 |
| WO | 0247575 A2 | 6/2002 |
| WO | 02060352 | 8/2002 |
| WO | 03030776 A2 | 4/2003 |
| WO | 03047468 A1 | 6/2003 |
| WO | 2004019825 A1 | 3/2004 |
| WO | 2005084595 A1 | 9/2005 |
| WO | 2006032051 A2 | 3/2006 |
| WO | 2006111391 A1 | 10/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2010121076 A2 | 10/2010 |

* cited by examiner

STEERABLE CATHETER

CROSS-REFERENCE TO RELATED APPLICATION

This application claims the benefit of U.S. Application No. 62/574,875, filed Oct. 20, 2017, which is incorporated by reference herein.

FIELD

The present application pertains generally to steerable endovascular delivery devices and related methods.

BACKGROUND

Endovascular delivery devices are used in various procedures to deliver prosthetic medical devices or instruments to locations inside the body that are not readily accessible by surgery or where access without surgery is desirable. Access to a target location inside the body can be achieved by inserting and guiding the delivery device through a pathway or lumen in the body, including, but not limited to, a blood vessel, an esophagus, a trachea, any portion of the gastrointestinal tract, a lymphatic vessel, to name a few. In one specific example, a prosthetic heart valve can be mounted in a crimped state on the distal end of a delivery device and advanced through the patient's vasculature (e.g., through a femoral artery and the aorta) until the prosthetic valve reaches the implantation site in the heart. The prosthetic valve is then expanded to its functional size such as by inflating a balloon on which the prosthetic valve is mounted, or by deploying the prosthetic valve from a sheath of the delivery device so that the prosthetic valve can self-expand to its functional size.

The usefulness of delivery devices is largely limited by the ability of the device to successfully navigate through small vessels and around tight bends in the vasculature, such as around the aortic arch. Various techniques have been employed to adjust the curvature of a section of a delivery device to help "steer" the prosthetic valve through bends in the vasculature. Nevertheless, there is a continued need for improved delivery devices.

SUMMARY

Disclosed herein are steerable catheter devices and related methods, which can be used to deliver a medical device, tools, agents, or other therapy to a location within a body of a subject. In some implementations, the steerable catheter devices can be used to deliver a medical device through the vasculature, such as to a heart of the subject.

Certain embodiments of the disclosure concern a steerable medical apparatus that includes a shaft having a proximal portion and a distal portion. The delivery apparatus can include a first pull wire having a proximal end and a distal end, and the distal end of the first pull wire can be coupled to the distal portion of the shaft. The delivery apparatus can include a second pull wire having a proximal end and a distal end, and the distal end of the second pull wire can be coupled to the distal portion of the shaft. The delivery apparatus can include a handle coupled to the proximal portion of the shaft. The handle can have a steering mechanism, which includes a first wheel and a second wheel operatively coupled by a differential mechanism. The proximal end of the first pull wire can be coupled to the first wheel, and the proximal end of the second pull wire can be coupled to the second wheel. Rotating both the first and second wheels in a first rotational direction can increase tension in the first and second pull wires such that the distal portion of the shaft curves in a first angular direction in a first plane. Further, rotating only the first wheel in the first rotational direction results in rotation of the second wheel in a second rotational direction opposite the first rotational direction, increasing tension in the first pull wire and decreasing tension in the second pull wire such that the distal portion of the shaft curves in a second angular direction away from the first plane.

In some embodiments, rotating both the first and second wheels in the second rotational direction can decrease tension in the first and second pull wires such that the distal portion of the shaft curves in a third angular direction opposite the first angular direction in the first plane.

In some embodiments, rotating only the second wheel in the first rotational direction can result in rotation of the first wheel in the second rotational direction, increasing tension in the second pull wire and decreasing tension in the first pull wire such that the distal portion of the shaft curves in a fourth angular direction opposite the second angular direction away from the first plane.

In some embodiments, the distal ends of the first and second pull wires can be spaced angularly apart from each other by 180 degrees.

In some embodiments, the second angular direction and the fourth angular direction can be in a second plane that is substantially normal to the first plane.

In some embodiments, the distal end of the first pull wire and the distal end of the second pull wire are spaced an equal distance from a distal end of the shaft.

In some embodiments, the delivery apparatus can further include a first pull-wire conduit and a second pull-wire conduit, each of which extends at least partially through the proximal and distal portions of the shaft. The first pull wire can extend through the first pull-wire conduit and the second pull wire can extend through the second pull-wire conduit.

In some embodiments, the handle can include a first actuation mechanism operatively coupled to the steering mechanism such that operating the first actuation mechanism can selectively rotate both the first and second wheels in the first or second rotational direction.

In some embodiments, the handle can include a second actuation mechanism operatively coupled to the steering mechanism such that operating the second actuation mechanism can selectively rotate only the first or second wheel in the first rotational direction.

In some embodiments, the distal end of the first pull wire and the distal end of the second pull wire can be spaced angularly apart from each other by an angle with respect to a longitudinal axis of the shaft, and the angle can be greater than zero degree and less than 180 degrees.

Certain embodiments of the disclosure concern also concern a steerable medical apparatus that includes a shaft, a first pull wire, a second pull wire, a steering mechanism, and an actuation mechanism. The shaft can include a proximal portion and a distal portion. The first pull wire can have a proximal end and a distal end, wherein the distal end of the first pull wire is coupled to the distal portion of the shaft. The second pull wire can have a proximal end and a distal end, wherein the distal end of the second pull wire is coupled to the distal portion of the shaft. The steering mechanism can include a first wheel and a second wheel operatively coupled by a differential mechanism. The proximal end of the first pull wire can be coupled to the first wheel, and the proximal end of the second pull wire can be coupled to the second wheel. The actuation mechanism can be operably coupled to the steering mechanism. Actuating the actuation mechanism in a first operational mode can rotate the first and second wheels in same direction and cause the distal portion of the shaft to curve in a first plane. Actuating the actuation mechanism in a second operational mode can rotate the first and second wheels in opposite directions and cause the distal portion of the shaft to curve away from the first plane.

In certain embodiments, rotating both the first and second wheels in a first rotational direction can increase tension in the first and second pull wires such that the distal portion of the shaft curves in a first angular direction in the first plane.

In certain embodiments, rotating both the first and second wheels in a second rotational direction opposite the first rotational direction can decrease tension in the first and second pull wires such that the distal portion of the shaft curves in a second angular direction opposite the first angular direction in the first plane.

In certain embodiments, rotating only the first wheel in a first rotational direction can result in rotation of the second wheel in a second rotational direction opposite the first rotational direction, increasing tension in the first pull wire and decreasing tension in the second pull wire such that the distal portion of the shaft curves in a first angular direction away from the first plane.

In certain embodiments, rotating only the second wheel in the first rotational direction can result in rotation of the first wheel in the second rotational direction, increasing tension in the second pull wire and decreasing tension in the first pull wire such that the distal portion of the shaft curves in a second angular direction opposite the first angular direction away from the first plane.

In certain embodiments, actuating the actuation mechanism in the second operational mode can cause the distal portion of the shaft to curve in a second plane that is normal to the first plane.

Also disclosed herein are methods of steering a delivery apparatus in a subject's vasculature. The method includes actuating a differential mechanism of the delivery apparatus to curve a distal portion of a shaft of the delivery apparatus in a first plane, and actuating the differential mechanism to curve the distal portion of the shaft in a direction away from the first plane.

In certain embodiments, the differential mechanism can operatively couple a first wheel and a second wheel. The first wheel can be coupled to a first pull wire and the second wheel can be coupled to a second pull wire.

In certain embodiments, the act of actuating the differential mechanism to curve the distal portion of the shaft of the delivery apparatus in the first plane can include rotating both the first and second wheels in a first rotational direction so as to increase tension in the first and second pull wires such that the distal portion of the shaft can curve in a first angular direction in the first plane.

In certain embodiments, the act of actuating the differential mechanism to curve the distal portion of the shaft of the delivery apparatus in the first plane can further include rotating both the first and second wheels in a second rotational direction opposite the first rotational direction so as to decrease tension in the first and second pull wires such that the distal portion of the shaft can curve in a second angular direction opposite the first angular direction in the first plane.

In certain embodiments, the act of actuating the differential mechanism to curve the distal portion of the shaft in a direction away from the first plane can include rotating only the first wheel in a first rotational direction, causing rotation of the second wheel in a second rotational direction opposite the first rotational direction, thereby increasing tension in the first pull wire and decreasing tension in the second pull wire such that the distal portion of the shaft can curve in a first angular direction away from the first plane.

In certain embodiments, the act of actuating the differential mechanism to curve the distal portion of the shaft in a direction away from the first plane can further include rotating only the second wheel in the first rotational direction, causing rotation of the first wheel in the second rotational direction, thereby increasing tension in the second pull wire and decreasing tension in the first pull wire such that the distal portion of the shaft can curve in a second angular direction away from the first plane.

In certain embodiments, the act of actuating the differential mechanism to curve the distal portion of the shaft in the direction away from the first plane can cause the distal portion of the shaft to curve in a second plane that is perpendicular to the first plane.

The foregoing and other objects, features, and advantages of the invention will become more apparent from the following detailed description, which proceeds with reference to the accompanying figures.

DETAILED DESCRIPTION

In particular embodiments, a steerable medical apparatus that can be used to deliver a medical device, tools, agents, or other therapy to a location within the body of a subject can include one or more steerable catheters and/or sheaths. Examples of procedures in which steerable catheters and sheaths are useful include cardiovascular, neurological, urological, gynecological, fertility (e.g., in vitro fertilization, artificial insemination), laparoscopic, arthroscopic, transesophageal, transvaginal, transvesical, transrectal, and procedures including access in any body duct or cavity. Particular examples include placing implants, including stents, grafts, embolic coils, and the like; positioning imaging devices and/or components thereof, including ultrasound transducers; and positioning energy sources, for example, for performing lithotripsy, RF sources, ultrasound emitters, electromagnetic sources, laser sources, thermal sources, and the like. In particular embodiments, the steerable medical apparatus is a delivery apparatus that is configured to deliver an implantable medical device, such as a prosthetic heart valve, through a patient's vasculature to the heart of a patient. Thus, the following description proceeds with reference to a steerable delivery apparatus. However, it should be understood that the embodiments disclosed herein can be incorporated in any steerable medical apparatus that is insertable into a patient's body for performing a medical procedure on the patient.

In some embodiments, the delivery apparatus includes a steerable shaft such as a guide sheath having one or more delivery catheters coaxially disposed within the guide sheath. In certain configurations, the delivery catheters can comprise one or more balloons or another type of expansion device at or near a distal end portion thereof for expanding an implantable medical device, such as a prosthetic heart valve.

Typically, a delivery device employs a pull wire having a distal end fixedly secured to a steerable section and a proximal end operatively connected to an adjustment knob located on a handle of the delivery device outside the body. The pull wire is typically disposed in a pull-wire lumen that extends longitudinally in or adjacent to a wall of the delivery device, for example, a sheath or catheter. Adjusting the adjustment knob, for example, rotating the knob, applies a pulling force on the pull wire, which in turn causes the steerable section to bend.

Some delivery devices employ multiple pull wires in order to enable curving the steerable section in multi-dimensions. For example, some delivery devices have two pull wires, each of which has a distal end fixedly coupled to the steerable section, and the distal end of the two pull wires are spaced angularly apart from one another. The proximal end of each pull wire can be operatively connected to a respective adjustment knob on the handle to adjust the pull wire's tension. As such, tensioning both pull wires can flex the steerable section in a first plane (e.g., curving backward toward the handle), whereas increasing tension in one of the pull wires while releasing tension in the other pull wire can flex the steerable section in a second plane (e.g., curving sideway) that transverses the first plane.

One problem of many delivery devices with dual pull-wires is that each pull wire must be adjusted independently in order to flex the steerable section in a desired direction. For example, to flex the steerable section in the first plane, it can be difficult to ensure equal tension is applied to both pull wires. To flex the steerable section in the second plane, the tension increase in one pull wire may not be appropriately compensated by the tension decrease in the other pull wire. Accordingly, steering accuracy of the delivery device can be difficult to control. Further, having independent adjustment mechanisms for the two pull wires can increase the design complexity and dimensional profile of the delivery device. Thus, a need exists for a delivery device with improved design and steerability.

Figure 1:
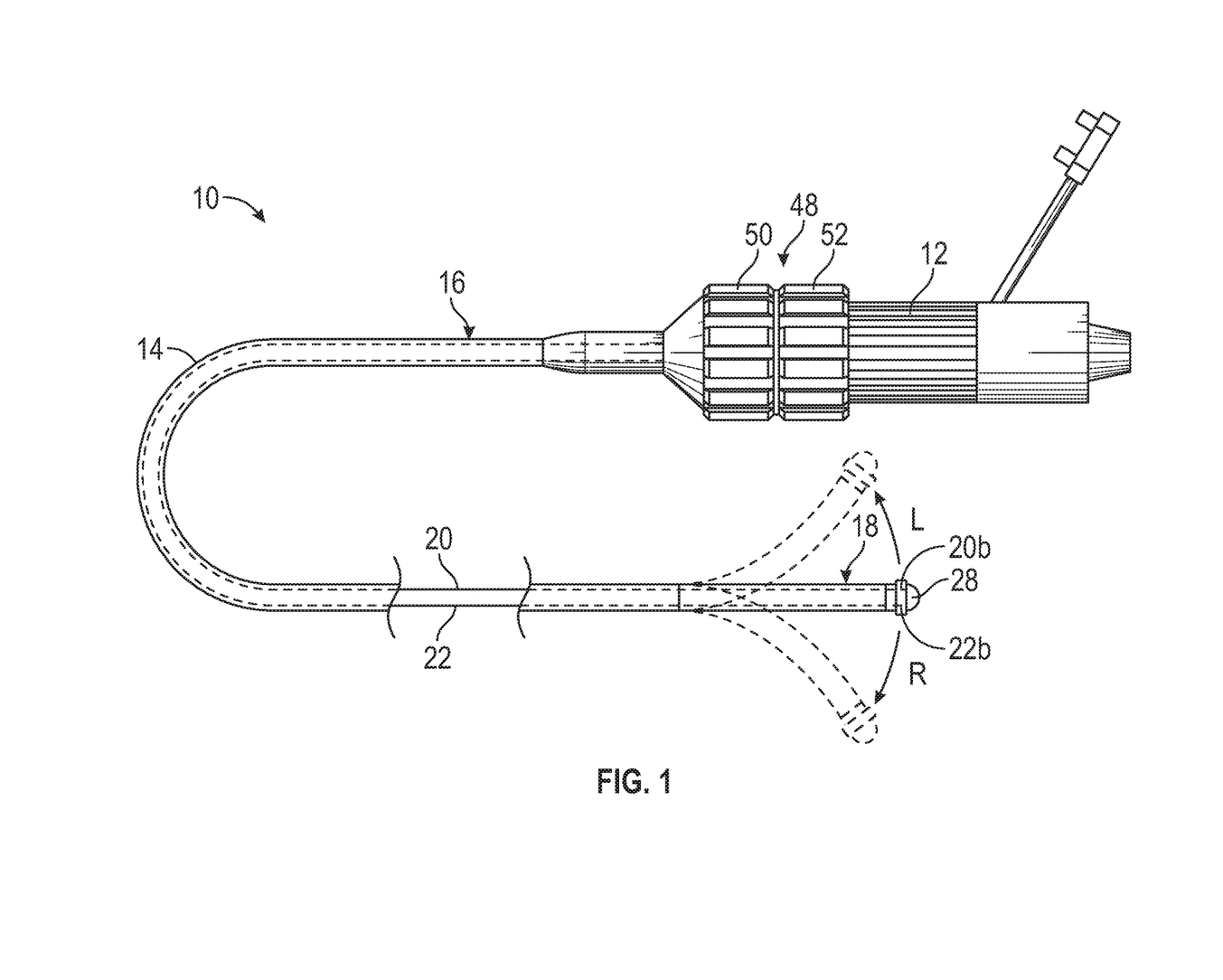
FIG. 1 shows a perspective view of a representative delivery apparatus, according to one embodiment.

Referring to FIG. 1, a delivery apparatus 10, according to one embodiment, comprises a handle 12 and a shaft 14 extending distally therefrom. The shaft 14 has a proximal portion 16 and a distal portion 18. The proximal portion 16 of the shaft 14 can be coupled to the handle 12. The handle 12 can be configured to position and/or manipulate the shaft 14, as further described below.

Although not shown, the delivery apparatus 10 can include one or more catheters coaxially disposed within and/or surrounding and movable relative to the shaft 14. For example, the delivery apparatus 10 can include an outer sheath extending over and longitudinally movable relative to the shaft 14. The delivery apparatus can also have an inner catheter configured as an implant catheter coaxially disposed within and movable relative to the central lumen 30 of the shaft 14, and the implant catheter can have a balloon-inflatable or self-expandable prosthetic heart valve mounted on a distal end of the implant catheter. Exemplary configurations of the prosthetic heart valve and implant catheter are further disclosed in U.S. Patent Application Publication Nos. 2013/0030519, 2012/0123529, 2010/0036484, 2010/0049313, 2010/0239142, 2009/0281619, 2008/0065011, and 2007/0005131, the disclosures of which are incorporated by reference. In addition, it should be understood that the delivery apparatus 10 can be used to deliver any of various other implantable devices, such as docking devices, leaflet clips, etc.

Figure 2:
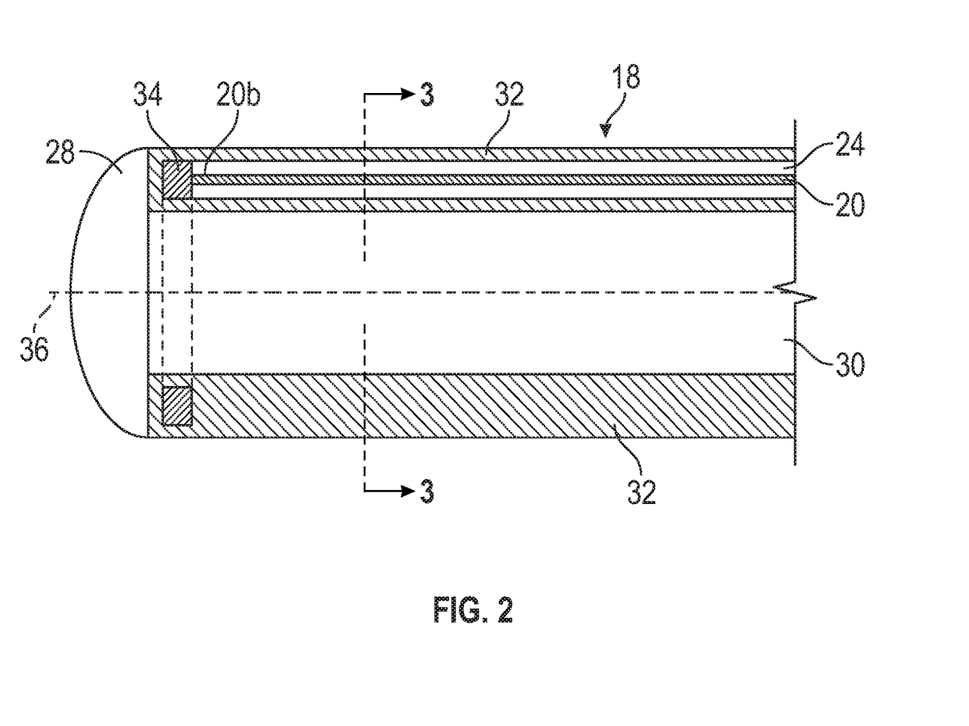
FIG. 2 shows a cross-sectional side elevation view of a distal portion of the delivery apparatus depicted in FIG. 1.

Referring to FIG. 2, the shaft 14 can have a central lumen 30 enclosed by a side wall 32. The side wall 32 of the shaft 14 can, in some embodiments, be made of a flexible, axially-non-compressible material and/or structure. In some embodiments, the shaft 14 can be an extruded polymer tube that is extruded to form the central lumen and the side wall 32. In another embodiment, the side wall 32 can comprise a helical coil, which desirably is a closed pitch coil without spacing between adjacent turns of the coil to avoid axial compression of the coil. The coil can be made of any suitable biocompatible metal, polymer, or combination thereof. The shaft can include an inner polymer layer extending over the inner surface of the coil and/or an outer polymer layer extending over the outer surface of the coil.

In alternative embodiments, the side wall 32 can comprise an elongated slotted tube (e.g., a metal tube) that has a plurality of axially-spaced, circumferentially extending slots formed (such as by laser cutting) along the length of the tube. Exemplary configurations of the slotted tube are described in U.S. Patent Application Publication No. 2015/0305865, which is incorporated herein by reference.

In another example, the side wall 32 can comprise a polymeric tube reinforced with a braided metal layer, such as polyimide tube reinforced with a braided stainless steel layer. In some embodiments, an inner polymeric layer can be secured to the inner surface of the braided layer and/or an outer polymeric layer can be secured to the outer surface of the braided layer.

Figure 3A:
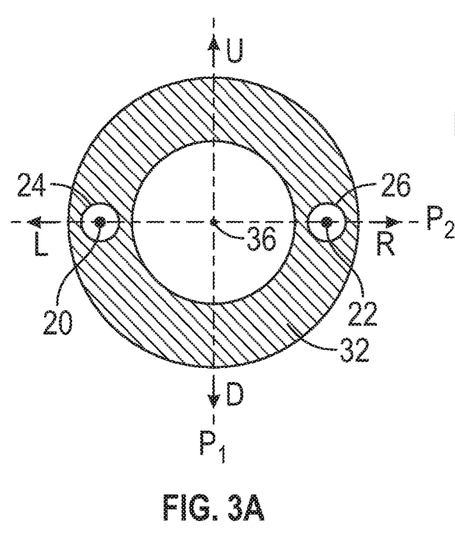
FIG. 3A shows a cross-sectional view of the delivery apparatus depicted in FIG. 1, taken along line 3-3 of FIG. 2, according to one embodiment.
Figure 3B:
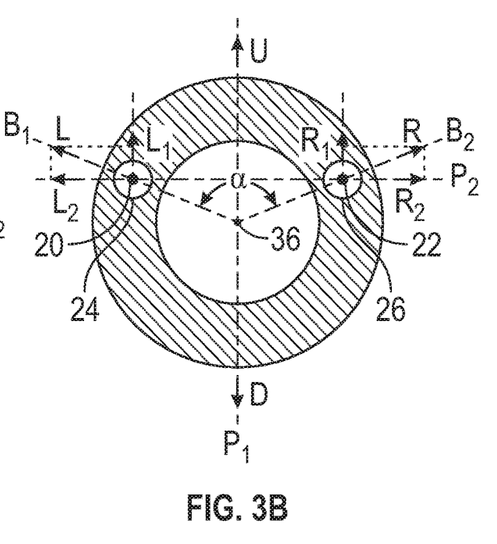
FIG. 3B shows a cross-sectional view of the delivery apparatus depicted in FIG. 1, taken along line 3-3 of FIG. 2, according to another embodiment.

As shown in FIGS. 2 and 3A-3B, the shaft 14 can further comprise a plurality of pull wires 20, 22 disposed in and extending longitudinally through respective pull-wire conduits 24, 26 formed in the side wall 32. The pull wires 20, 22 can be used to control and/or manipulate the curvature of the distal portion 18 of the shaft 14. The pull-wire conduits 24, 26 can extend at least partially through the proximal portion 16 and distal portion 18 of the shaft 14.

As shown in FIGS. 3A-3B, the pull-wire conduits 24, 26 can be eccentrically disposed relative to the central lumen 30 and circumferentially spaced relative to each other at the distal portion 18 of the shaft 14.

In some embodiments, the pull-wire conduits 24, 26 are spatially separated from each other through the entire length of the shaft 14. Alternatively, the pull-wire conduits 24, 26 can be merged together at the proximal portion 16 of the shaft 14 but branch out separately at the distal portion 18 of the shaft 14. In other words, the pull wires 20, 22 can share the same lumen along the proximal portion 16 of the shaft 14 but extend through separate, longitudinally extending pull-wire conduits 24, 26 at the distal portion 18 of the shaft 14.

In other embodiments, the pull-wire conduits 24, 26 may have openings on the side wall 32 of the shaft 14 near the proximal portion 16, so that the proximal portions of the pull wires 20, 22 may extend outside the shaft 14 through such openings before connecting to a steering mechanism 38 located inside the handle 12. Other configurations of the pull-wire conduits are described in U.S. Patent Application Publication No. 2016/0158497, which is incorporated herein by reference. Regardless of the configuration of the pull-wire conduits 24, 26 at the proximal portion 16, the pull-wire conduits 24, 26 can be substantially parallel to each other along the distal portion 18 of the shaft 14.

In some embodiments, the central lumen 30 and/or the pull-wire conduits 24, 26 can have a low-friction and/or flexible liner (not shown) covering the inner surface of the lumen/conduit, and the liner can comprise polytetrafluoroethylene (PTFE), ultra-high-molecular-weight polyethylene (UHMWPE), or another suitable material.

A proximal end 20a of the first pull wire 20 and a proximal end 22a of the second pull wire 22 can be connected to a steering mechanism 38 of the handle 12. As described more fully below, the steering mechanism 38 can be configured to selectively increase and/or decrease tension in the pull wires 20, 22 to, for example, adjust the curvature of the distal portion 18 of the shaft 14.

In some embodiments, the distal portion 18 of the shaft 14 can be constructed from a relatively more flexible material than the proximal portion 16 of the shaft 14 and/or can otherwise be constructed to be relatively more flexible than the proximal portion 16 of the shaft 14 such that the curvature of the proximal portion 16 can remain substantially unchanged when the curvature of the distal portion 18 is adjusted by applying tension thereto by the pull wires 20, 22, as further described below. Further details of the construction of the shaft 14, the handle 12, and/or adjusting tension in a pull wire are described in U.S. Patent Application Publication Nos. 2013/0030519, 2009/0281619, 2008/0065011, and 2007/0005131, which are incorporated by reference herein.

Referring to FIG. 2, the distal end 28 of the shaft 14 can be formed as a low durometer atraumatic tip, which can, in certain embodiments, be radiopaque. A distal end 20b of the first pull wire 20 and a distal end 22b of the second pull wire 22 can be coupled to the distal portion 18 of the shaft 14. In certain embodiments, the distal end 20b of the first pull wire 20 and the distal end 22b of the second pull wire 22 can be coupled to the same or at least substantially the same axially location at the distal end 28 of the shaft 14. For example, in some embodiments, the distal ends 20b, 22b of the pull wires 20, 22 can be fixedly secured to a pull ring 34 that is proximally adjacent to the distal end 28 of the shaft 14. The pull ring 34, which can be coaxial with the distal portion 18 of the shaft 14, can be embedded or otherwise secured to the shaft 14 at or adjacent to the distal ends of the pull-wire conduits 24, 26.

FIGS. 3A-3B shows exemplary embodiments of the angular positioning of the pull-wire conduits 24, 26 (and thus the pull wires 20, 22) along the distal portion 18 of the shaft 14. In the illustrated embodiments, the pull-wire conduits 24, 26 are disposed within the side wall 32 of the shaft 14. In other embodiments, the pull-wire conduits 24, 26 can have a different location, for example, adjacent to an interior or exterior surface of the side wall 32.

Along the distal portion 18 of the shaft 14, the first pull-wire conduit 24 can be positioned along a first axis $B_1$ extending radially from the central axis 36 of the shaft 14 to the first pull-wire conduit 24. The second pull-wire conduit 26 can be positioned along a second axis $B_2$ extending radially from the central axis 36 of the shaft 14 to the second pull-wire conduit 26. As shown, the pull-wire conduits 24, 26 can be spaced angularly apart from one another by an angle ($\alpha$) between axes $B_1$ and $B_2$.

In the embodiment depicted in FIG. 3A, the angle $\alpha$ can be about 180 degrees (i.e., the distal ends 20b, 22b of the pull wires 20, 22 are diametrically opposed to each other with respect to the central axis 36).

In the other embodiment depicted in FIG. 3B, the angle $\alpha$ can be any angle greater than zero degrees and less than 180 degrees. In some embodiments, the angle $\alpha$ can be between about 90 degrees and about 150 degrees. In the embodiment shown, the angle $\alpha$ is about 120 degrees.

As described more fully below, the dual-wire configurations as depicted in FIGS. 3A-3B allow the distal portion 18 of the shaft 14 to flex in various directions on multiple planes in a three-dimensional (3D) space, so as to accurately and conveniently position and align the distal end 28 (and the atraumatic tip) of the shaft 14.

Figure 4:
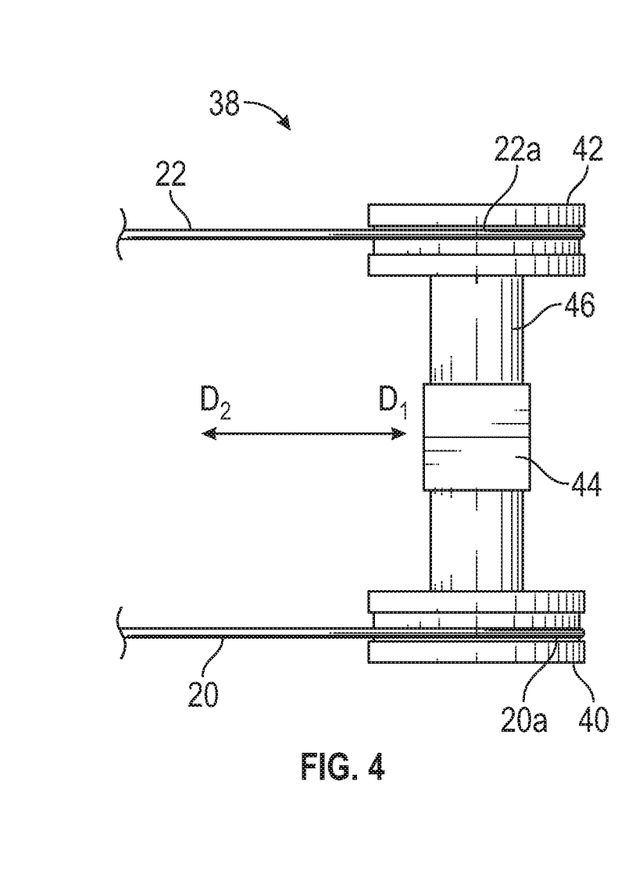
FIG. 4 shows a top plan view of a steering mechanism included in the handle of the delivery apparatus depicted in FIG. 1.
Figure 5:
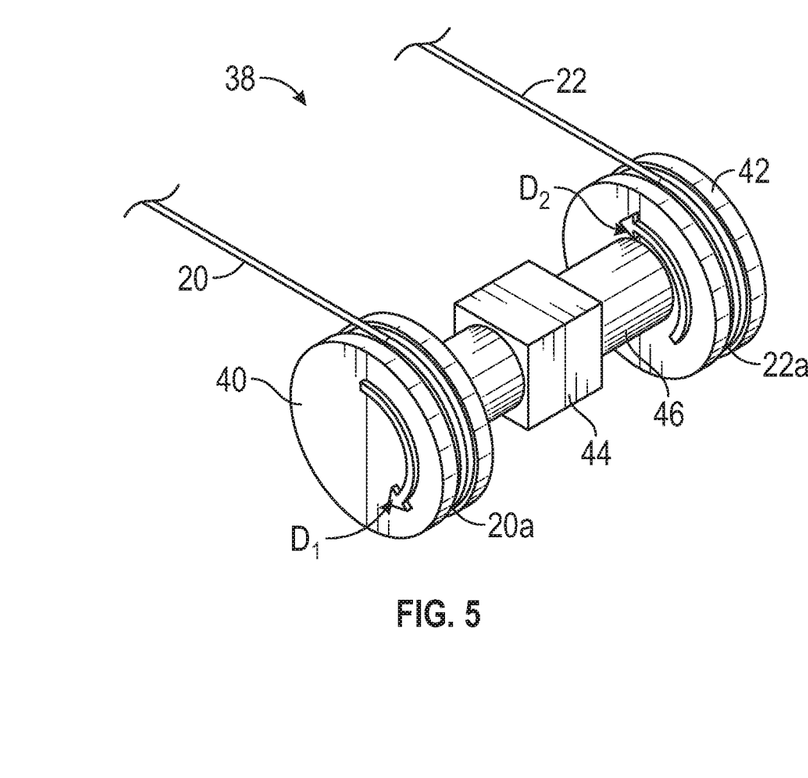
FIG. 5 shows a perspective view of the steering mechanism depicted in FIG. 4.

Referring to FIGS. 4-5, the operation of the steering mechanism 38 is illustrated. As noted above, the proximal ends 20a, 22a of the pull wires 20, 22 can be coupled to the steering mechanism 38. In some embodiments, the steering mechanism can be disposed inside of the handle 12.

The steering mechanism 38 can include a first spool or wheel 40 and a second spool or wheel 42 connected by an axle 46. Specifically, the first and second wheels 40, 42 can be operatively coupled by a differential mechanism 44 located on the axle 46.

The differential mechanism 44 can include a drive shaft, a first output shaft, a second output shaft, and a gear train coupling the drive shaft and the first and second output shafts. The differential mechanism 44 can, for example, allow the first and second output shafts to be rotated together and/or individually. The differential mechanism 44 can, for example, allow the first and second output shafts to be rotated together in the same direction and/or in opposite directions relative to each other. The differential mechanism 44 can be constructed and/or implemented by a variety of means and it can be either passive or active. For example, in some embodiments, the differential mechanism 44 can be an open differential, a locking (e.g., selectively lockable) differential, or a limited-slip differential. As described herein, all known differentials can be used in the steering mechanism 38, and they are considered to be within the scope of the present disclosure.

In one particular embodiment, the first output shaft of the differential mechanism 44 can be coupled to the first wheel 40, and the second output shaft of the differential mechanism 44 can be coupled to the second wheel 42. As such, the steering mechanism 38 can adjust the tension of the first and second pull wires 20, 22 by selectively rotating the first and second wheels 40, 42.

As shown in FIG. 4, the proximal end 20a of the first pull wire 20 can be coupled to the first wheel 40, and the proximal end 22a of the second pull wire 22 can be coupled to the second wheel 42. The first and second pull wires 20, 22 can be respectively spooled or wound around the first and second wheels 40, 42. In the illustrated embodiments, pull wires 20, 22 are generally spooled or wound in the same direction, e.g., either clockwise or counterclockwise.

In a first operational mode, generally equal tension can be applied to both pull wires 20, 22 by rotating both wheels 40, 42 in a same direction. This can be accomplished, for example, by rotating the drive shaft of the differential mechanism 44. In certain embodiments, a locking differential and/or limited slip differential can help maintain equal tension on both pull wire by ensuring that both wheels 40, 42 rotate together in the same direction as the drive shaft is rotated.

For example, as illustrated in FIG. 4, rotating both the first and second wheels 40, 42 in a first rotational direction $D_1$ (e.g., clockwise) can wind the pull wires 20, 22 onto the wheels 40, 42 so as to increase tension in the pull wires 20, 22. This can cause the distal portion 18 of the shaft 14 to curve in a first angular direction U in a first plane $P_1$, as shown in FIGS. 3A-3B.

Conversely, rotating both the first and second wheels 40, 42 in a second rotational direction $D_2$ (e.g., counter-clockwise) opposite the first rotational direction $D_1$ can unwind the pull wires 20, 22 from the wheels 40, 42 so as to decrease tension in the pull wires 20, 22. This can cause the distal portion 18 of the shaft 14 to return to a resting configuration of the shaft 14, by curving in a second angular direction D opposite the first angular direction U in the first plane $P_1$, as shown in FIGS. 3A-3B.

In lieu of or in addition to simultaneously adjusting tension in the pull wires 20, 22 by rotating the first and second wheels 40, 42 together in the same direction, tension in the pull wires 20, 22 can be simultaneously adjusted by longitudinally translating the steering mechanism 38 relative to the shaft 14. For example, the drive shaft of the differential mechanism 44 and/or an independent drive shaft connecting to the axle 46 can be configured to translate (e.g., slide) the axle 46 distally and/or proximally relative to the shaft 14. Because the first and second wheels 40, 42 are coupled by the axle 46, distal or proximal movement of the axle 46 results in corresponding distal or proximal movement of the wheels 40, 42. Because the proximal ends 20a, 22a of the pull wires 20, 22 are connected to the wheels 40, 42, proximal movement (e.g., longitudinal movement in the direction shown by arrow $D_1$ shown of FIG. 4) of the wheels 40, 42 relative to the shaft 14 can increase tension in the pull wires 20, 22, whereas distal movement (e.g., longitudinal movement in the direction shown by arrow $D_2$ of FIG. 4) of the wheels 40, 42 relative to the shaft can decrease tension in the pull wires 20, 22.

As noted above, the conduits 24, 26 can be substantially parallel to each other along the distal portion 18 of the shaft 14. Accordingly, the first and second pull wires 20, 22 at the distal portion 18 can be substantially parallel to each other such that they can define a second plane $P_2$.

For the embodiment depicted in FIG. 3A where the distal ends 20b, 22b of the pull wires 20, 22 are diametrically opposed to each other with respect to the central axis 36, the second plane $P_2$ can intersect the second plane $P_1$ at the central axis 36. Further, the second plane $P_2$ can be substantially normal to the first plane $P_1$.

The distal portion 18 of the shaft 14 can have a biased structure that enables the distal portion 18 to curve in the first angular direction U when both pull wires 20, 22 are tensioned. For example, side wall areas of the distal portion 18 facing the first angular direction U can have a lower durometer than the side wall areas on the opposite side (i.e., facing the second angular direction D). Various structures can be employed to achieve such durometer difference. For example, the opposing side walls of the distal portion 18 can be constructed by using different materials, or the same material having different densities, or different structures (e.g., the distal portion 18 can have a slotted tube portion where the slots are located on the side wall areas facing the first angular direction U), or any combination thereof.

For the embodiment depicted in FIG. 3B where the distal ends 20b, 22b of the pull wires 20, 22 are spaced angularly apart from each other by an angle less than 180 degrees, the second plane $P_2$ can intersect the first plane $P_1$ at a location that is eccentric to the central axis 36. Further, the second plane $P_2$ can be substantially normal to the first plane $P_1$.

The distal portion 18 of the shaft 14 can have an intrinsic bias to curve in the first angular direction U when both pull wires 20, 22 are tensioned. Because the distal ends 20b, 22b of the pull wires 20, 22 are disposed on the same side of the central axis 36 along the first angular direction U, tensioning both pull wires 20, 22 can generate a bending force away from the central axis 36 in the first angular direction U.

In certain embodiments, the distal portion 18 can be straight when it is in its neutral or resting configuration. Increasing tension on both pull wires 20, 22 can cause the distal portion 18 of the shaft 14 to flex in the first angular direction U, thus moving the distal end 28 of the shaft 14 slightly proximally toward the handle 12. On the other hand, releasing tension on pull wires 20, 22 can allow the distal portion 18 to straighten in the second angular direction D and move the distal end 28 of the shaft 14 slightly distally away from the handle 12.

In alternative embodiments (not shown), the distal portion 18 can be pre-curved (e.g., curving in the direction D) when it is in neutral configuration. In such embodiments, increasing tension on both pull wires 20, 22 can cause the distal portion 18 to straighten and/or flex in the direction U, while decreasing tension allows the distal portion 18 of the shaft 14 to return to its pre-curved, neutral configuration (e.g., curving in the direction D).

In a second operational mode, tension can be applied to only one of the pull wires 20, 22, whereas tension in the other pull wire is reduced. This can be accomplished, for example, by rotating the wheels 40, 42 in opposite directions such that winding of one pull wire is accompanied by unwinding of the other pull wire. As a result, the distal portion 18 of the shaft 14 can curve away from the first plane $P_1$.

For example, as illustrated in FIG. 5, due to the differential mechanism 44, rotating only the first wheel 40 in the first rotational direction $D_1$ (e.g., clockwise) can result in simultaneous rotation of the second wheel 42 in the second rotational direction $D_2$ (e.g., counter-clockwise) that is opposite the first rotational direction $D_1$. This can increase tension in the first pull wire 20 and decrease tension in the second pull wire 22. As a result, the distal portion 18 of the shaft 14 can curve in a first angular direction L away from the first plane $P_1$ (see e.g., FIGS. 3A-3B).

Conversely, rotating only the second wheel 42 in the first rotational direction $D_1$ (e.g., clockwise) can result in simultaneous rotation of the first wheel 40 in the second rotational direction $D_2$ (e.g., counter-clockwise). This can decrease tension in the first pull wire 20 and increase tension in the second pull wire 22. As a result, the distal portion 18 of the shaft 14 can curve in a second angular direction R away from the first plane $P_1$ (see e.g., FIGS. 3A-3B). The second angular direction R can be generally opposite the first angular direction L.

For the embodiment depicted in FIG. 3A where the distal ends 20b, 22b of the pull wires 20, 22 are diametrically opposed to each other with respect to the central axis 36, rotating the wheels 40, 42 in opposite directions can cause the distal portion 18 of the shaft 14 to curve in the second plane $P_2$ that is perpendicular to the first plane $P_1$. In other words, the first angular direction L and the second angular direction R can be within the second plane $P_2$, pointing to opposite directions (e.g., respectively to the left and right in FIG. 3A) away from the central axis 36.

For the embodiment depicted in FIG. 3B where the distal ends 20b, 22b of the pull wires 20, 22 are spaced angularly apart from each other by an angle less than 180 degrees, rotating the wheels 40, 42 in opposite directions can cause the distal portion 18 of the shaft 14 to curve away from the first plane P1 in a non-perpendicular fashion, due to the eccentricity of the pull wires 20, 22 relative to the central axis 36.

For example, the first angular direction L can be decomposed into a first component $L_1$ in the first plane $P_1$ (e.g., to the top in FIG. 3B) and a second component $L_2$ in the second plane $P_2$ (e.g., to the left in FIG. 3B). Similarly, the second angular direction R can be decomposed into a first component $R_1$ in the first plane $P_1$ (e.g., to the top in FIG. 3B) and a second component $R_2$ in the second plane $P_2$ (e.g., to the right in FIG. 3B). While the second components $L_2$ and $R_2$ are within the second plane $P_2$, pointing to opposite directions (e.g., respectively to the left and right in FIG. 3B) away from the central axis 36, the first components $L_1$ and $R_1$ are away from the second plane $P_2$, pointing to the same direction (e.g., to the top in FIG. 3B).

In certain embodiments, the distal portion 18 of the shaft 14 can be straight when it is in its neutral or resting configuration. Increasing tension in only one of the pull wires while simultaneously decreasing tension in the other pull wire can cause the distal portion 18 to curve in one angular direction (e.g., L or R) away from the first plane $P_1$. Reversing the tensioning and/or untensioning of the pull wires can allow the distal portion 18 of the shaft 14 to return to its straight configuration, and/or curve in the opposite angular direction away from the first plane $P_1$.

In alternative embodiments (not shown), the distal portion 18 can be pre-curved (e.g., curving toward direction L or R) when it is in its neutral configuration. Increasing tension in only one of the pull wires while simultaneously decreasing tension in the other pull wire can cause the distal portion 18 to flex in the opposite angular direction (e.g., R or L), causing the distal portion 18 to straighten or even curve toward the opposite side relative to its neutral, pre-curved configuration. Reversing the tensioning and/or untensioning of the pull wires can allow the distal portion 18 to return to its pre-curved configuration and/or even curve beyond its neutral, pre-curved configuration.

The delivery apparatus 10 can include an actuation mechanism 48, which can be positioned on the handle 12 and operably coupled to the steering mechanism 38. The actuation mechanism 48 can be operated in a plurality of operational modes. For example, actuating the actuation mechanism 48 in a first operational mode can rotate both wheels 40, 42 in the same direction and cause the distal portion 18 of the shaft 14 to curve in the first plane $P_1$, and actuating the actuation mechanism 48 in a second operational mode can rotate the wheels 40, 42 in opposite directions relative to each other and cause the distal portion 18 of the shaft 14 to curve away from the first plane $P_1$.

In the exemplary embodiment depicted in FIG. 1, the actuation mechanism 48 includes a first actuation mechanism 50 and a second actuation mechanism 52. The first actuation mechanism 50 can be operatively coupled to the steering mechanism 38 such that operating the first actuation mechanism 50 can selectively rotate both the first and second wheels 40, 42 in either the first or second rotational direction (i.e., $D_1$ or $D_2$). The second actuation mechanism 52 can be operatively coupled to the steering mechanism 38 such that operating the second actuation mechanism 52 can selectively rotate only one of the wheels 40, 42 in the first rotational direction $D_1$, resulting in simultaneous rotation of the other wheel in the second rotational direction $D_2$.

The user-interface of the first and second actuation mechanisms 50, 52 can take the form of rotatable knobs as depicted in FIG. 1. For example, clockwise (or counter-clockwise) rotation of the first actuation mechanism 50 can simultaneous increase the tension of both pull wires 20, 22; whereas, counter-clockwise (or clockwise) rotation of that knob can simultaneous decrease the tension of both pull wires 20, 22. In another example, clockwise (or counter-clockwise) rotation of the second actuation mechanism 52 can simultaneously increase the tension of the pull wire 20 and decrease the tension of the pull wire 22; whereas, counter-clockwise (or clockwise) rotation of that knob can simultaneously increase the tension of pull wire 22 and decrease the tension of pull wire 20.

It should be understood, however, that the user interface of actuation mechanism 48 can take any other forms, such as push buttons, joysticks, voice-controlled actuators, etc. Although the embodiment depicted in FIG. 1 shows two independent rotatable knobs, it should be understood that the user interface of the actuation mechanism 48 can be integrated into a single unit, or alternatively it can include a collection of more than two units. In one exemplary, non-limiting embodiment (not shown), the user interface of the actuation mechanism 48 can include four buttons: a first button configured to increase tension in both pull wires 20, 22; a second button configured to decrease tension in both pull wires 20, 22; a third button configured to increase tension in pull wire 20 and decrease tension in pull wire 22; and a fourth button configured to increase tension in pull wire 22 and decrease tension in pull wire 20.

Although not shown, it should be understood that the operational coupling between the actuation mechanism 48 and the steering mechanism 38 can also take a variety of forms. For example, the first actuation mechanism 50 can be coupled to the steering mechanism 38 by the drive shaft of the differential mechanism 44. Actuating the first actuation mechanism 50 can rotate the drive shaft and a drive gear inside the differential mechanism 44, thus causing the first and second output shafts to rotate clockwise or counter-clockwise. As a result, both wheels 40, 42 can rotate in the same direction as the first and second output shafts and can increase or decrease the tension of both pull wires 20, 22. Alternatively, the first actuation mechanism 50 can directly increase or decrease the tension of both pull wires 20, 22 by simultaneously winding or unwinding those wires on respective wheels 40, 42. The second actuation mechanism 52 can be coupled to the steering mechanism 38 such that it can selectively drive only one of the output shafts and/or wheels 40, 42. For example, the second actuation mechanism 52 can be configured to drive only one wheel in one rotational direction ($D_1$ or $D_2$), causing the other wheel to rotate in opposite direction due to the differential mechanism 44.

In some embodiments, the delivery apparatus 10 can further include at least two sensors (not shown) that respectively measure the tension force in each of the pull wires 20, 22. Those sensors can be operatively coupled to one or more indicators (not shown) positioned on the handle 12. The indicators can take a variety of forms, such as needle indicators, LED lights, digital display, etc. Such indicators can be used to provide user-perceivable feedback and information to the operator about the tension of each pull wire measured by respective sensors. Thus, the operator can precisely control the flexing of the distal portion 18 of the shaft 14 by adjusting the tension of each pull wire through the actuation mechanism 48.

General Considerations

It should be understood that the disclosed embodiments can be adapted to deliver and implant prosthetic devices in any of the native annuluses of the heart (e.g., the pulmonary, mitral, and tricuspid annuluses), and can be used with any of various delivery approaches (e.g., retrograde, antegrade, transseptal, transventricular, transatrial, etc.).

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved. The technologies from any example can be combined with the technologies described in any one or more of the other examples. In view of the many possible embodiments to which the principles of the disclosed technology may be applied, it should be recognized that the illustrated embodiments are only preferred examples and should not be taken as limiting the scope of the disclosed technology.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "connected" generally mean electrically, electromagnetically, and/or physically (e.g., mechanically or chemically) coupled or linked and does not exclude the presence of intermediate elements between the coupled or associated items absent specific contrary language.

Directions and other relative references (e.g., inner, outer, etc.) may be used to facilitate discussion of the drawings and principles herein, but are not intended to be limiting. For example, certain terms may be used such as "inside," "outside,", "interior," "exterior," and the like. Such terms are used, where applicable, to provide some clarity of description when dealing with relative relationships, particularly with respect to the illustrated embodiments. Such terms are not, however, intended to imply absolute relationships, positions, and/or orientations. As used herein, "and/or" means "and" or "or", as well as "and" and "or".

In view of the many possible embodiments to which the principles of the disclosure may be applied, it should be recognized that the illustrated embodiments are only examples and should not be taken as limiting the scope of the claimed subject matter. Rather, the scope of the claimed subject matter is defined by the following claims and their equivalents.

The invention claimed is:

1. A steerable medical apparatus, comprising:
a shaft comprising a proximal portion and a distal portion;
a first pull wire having a proximal end and a distal end, wherein the distal end of the first pull wire is coupled to the distal portion of the shaft;
a second pull wire having a proximal end and a distal end, wherein the distal end of the second pull wire is coupled to the distal portion of the shaft; and
a handle coupled to the proximal portion of the shaft and comprising a steering mechanism, wherein the steering mechanism comprises a first wheel and a second wheel operatively coupled by a differential mechanism, the proximal end of the first pull wire is coupled to the first wheel, and the proximal end of the second pull wire is coupled to the second wheel,
wherein rotating both the first and second wheels in a first rotational direction increases tension in the first and second pull wires such that the distal portion of the shaft curves in a first angular direction in a first plane,
wherein rotating only the first wheel in the first rotational direction results in rotation of the second wheel in a second rotational direction opposite the first rotational direction, increasing tension in the first pull wire and decreasing tension in the second pull wire such that the distal portion of the shaft curves in a second angular direction away from the first plane.

2. The apparatus of claim 1, wherein rotating both the first and second wheels in the second rotational direction decreases tension in the first and second pull wires such that the distal portion of the shaft curves in a third angular direction opposite the first angular direction in the first plane.

3. The apparatus of claim 1, wherein rotating only the second wheel in the first rotational direction results in rotation of the first wheel in the second rotational direction, increasing tension in the second pull wire and decreasing tension in the first pull wire such that the distal portion of the shaft curves in a fourth angular direction opposite the second angular direction away from the first plane.

4. The apparatus of claim 3, wherein the distal ends of the first and second pull wires are spaced angularly apart from each other by 180 degrees.

5. The apparatus of claim 4, wherein the second angular direction and the fourth angular direction are in a second plane that is substantially normal to the first plane.

6. The apparatus of claim 1, wherein the distal end of the first pull wire and the distal end of the second pull wire are spaced an equal distance from a distal end of the shaft.

7. The apparatus of claim 1, further comprising a first pull-wire conduit and a second pull-wire conduit, each of which extends at least partially through the proximal and distal portions of the shaft, wherein the first pull wire extends through the first pull-wire conduit and the second pull wire extends through the second pull-wire conduit.

8. The apparatus of claim 1, wherein the handle comprises a first actuation mechanism operatively coupled to the steering mechanism such that operating the first actuation mechanism can selectively rotate both the first and second wheels in the first or second rotational direction.

9. The apparatus of claim 1, wherein the handle comprises a second actuation mechanism operatively coupled to the steering mechanism such that operating the second actuation mechanism can selectively rotate only the first or second wheel in the first rotational direction.

10. The apparatus of claim 1, wherein the distal end of the first pull wire and the distal end of the second pull wire are spaced angularly apart from each other by an angle with respect to a longitudinal axis of the shaft, wherein the angle is greater than zero degree and less than 180 degrees.

11. A steerable medical apparatus, comprising:
a shaft comprising a proximal portion and a distal portion;
a first pull wire having a proximal end and a distal end, wherein the distal end of the first pull wire is coupled to the distal portion of the shaft;
a second pull wire having a proximal end and a distal end, wherein the distal end of the second pull wire is coupled to the distal portion of the shaft;
a steering mechanism comprising a first wheel and a second wheel operatively coupled by a differential mechanism, wherein the proximal end of the first pull wire is coupled to the first wheel, and the proximal end of the second pull wire is coupled to the second wheel; and
an actuation mechanism operably coupled to the steering mechanism,
wherein actuating the actuation mechanism in a first operational mode rotates the first and second wheels in same direction and causes the distal portion of the shaft to curve in a first plane,
wherein actuating the actuation mechanism in a second operational mode rotates the first and second wheels in opposite directions and causes the distal portion of the shaft to curve away from the first plane.

12. The apparatus of claim 11, wherein rotating both the first and second wheels in a first rotational direction increases tension in the first and second pull wires such that the distal portion of the shaft curves in a first angular direction in the first plane.

13. The apparatus of claim 12, wherein rotating both the first and second wheels in a second rotational direction opposite the first rotational direction decreases tension in the first and second pull wires such that the distal portion of the shaft curves in a second angular direction opposite the first angular direction in the first plane.

14. The apparatus of claim 11, wherein rotating only the first wheel in a first rotational direction results in rotation of the second wheel in a second rotational direction opposite the first rotational direction, increasing tension in the first pull wire and decreasing tension in the second pull wire such that the distal portion of the shaft curves in a first angular direction away from the first plane.

15. The apparatus of claim 14, wherein rotating only the second wheel in the first rotational direction results in rotation of the first wheel in the second rotational direction, increasing tension in the second pull wire and decreasing tension in the first pull wire such that the distal portion of the shaft curves in a second angular direction opposite the first angular direction away from the first plane.

16. The apparatus of claim 11, wherein the distal end of the first pull wire and the distal end of the second pull wire are spaced an equal distance from a distal end of the shaft.

17. The apparatus of claim 11, further comprising a first pull-wire conduit and a second pull-wire conduit, each of which extends at least partially through the proximal and distal portions of the shaft, wherein the first pull wire extends through the first pull-wire conduit and the second pull wire extends through the second pull-wire conduit.

18. The apparatus of claim 11, wherein the distal end of the first pull wire and the distal end of the second pull wire are spaced angularly apart from each other by an angle with respect to a longitudinal axis of the shaft, wherein the angle is greater than zero degree and less than 180 degrees.

19. The apparatus of claim 11, wherein the distal end of the first pull wire and the distal end of the second pull wire are spaced angularly apart from each other by 180 degrees.

20. The apparatus of claim 19, wherein actuating the actuation mechanism in the second operational mode causes the distal portion of the shaft to curve in a second plane that is normal to the first plane.

* * * * *